US009198953B2

(12) United States Patent
Cheng et al.

(10) Patent No.: US 9,198,953 B2
(45) Date of Patent: Dec. 1, 2015

(54) METHOD FOR REPAIRING NEURODEGENERATION

(75) Inventors: Henrich Cheng, Taipei (TW); Ming-Jei Lo, Taipei (TW); Yee-Chiang Liu, Taipei (TW)

(73) Assignee: Eu Sol Biotech Co., Ltd., Taipei (TW)

( * ) Notice: Subject to any disclaimer, the term of this patent is extended or adjusted under 35 U.S.C. 154(b) by 475 days.

(21) Appl. No.: 12/856,086

(22) Filed: Aug. 13, 2010

(65) Prior Publication Data

US 2011/0039774 A1    Feb. 17, 2011

Related U.S. Application Data

(60) Provisional application No. 61/233,987, filed on Aug. 14, 2009.

(51) Int. Cl.
*A61K 38/18* (2006.01)
*A61K 9/00* (2006.01)
*A61K 47/42* (2006.01)

(52) U.S. Cl.
CPC .......... *A61K 38/1825* (2013.01); *A61K 9/0024* (2013.01); *A61K 47/42* (2013.01)

(58) Field of Classification Search
None
See application file for complete search history.

(56) References Cited

U.S. PATENT DOCUMENTS

| 6,074,663 | A * | 6/2000 | Delmotte et al. ............. 424/443 |
| 2002/0090678 | A1 | 7/2002 | Kordyum et al. | |
| 2002/0155532 | A1 | 10/2002 | Stegmann et al. | |
| 2004/0267289 | A1 * | 12/2004 | Cheng ............................ 606/152 |
| 2007/0134204 | A1 | 6/2007 | Cheng et al. | |
| 2008/0109035 | A1 * | 5/2008 | Cheng ............................ 606/214 |
| 2008/0119403 | A1 * | 5/2008 | Imamura et al. ............... 514/12 |
| 2009/0305988 | A1 * | 12/2009 | Cheng et al. .................... 514/12 |

FOREIGN PATENT DOCUMENTS

| WO | WO-93/08828 | 5/1993 |
| WO | WO 2007138236 A1 * | 12/2007 |

OTHER PUBLICATIONS

Fanciullacci et al. Clinical, urodynamic and neurophysiological findings in patients with neuropathic bladder due to a lumbar intervertebral disc protrusion. Paraplegia. Oct. 1989;27(5):354-8.*
Couch 2008 "Spontaneous intracranial hypotension: the syndrome and its complications" Curr Treat Options Neurol 10(1):3-11 (abstract only).*
Sasaki et al. 2003 "In vivo use of human fibrin glue under the subperiosteal and subcutaneous planes in Holtzman rats" Aesthet Surg J 23(6):458-63 (abstract).*
Tsai et al. 2008 "Involvement of acidic fibroblast growth factor in spinal cord injury repair processes revealed by a proteomics approach" Mol Cell Proteomics 7(9):1668-1687.*
Laird et al "Acidic Fibroblast Growth Factor (aFGF) Stimulates Rat Sciatic Nerve Regeneration After a Criish Injury" Journal of Physiology vol. 480, p. 69. 1994.
Harbaugh et al "Bilateral Peroneal Neuropathy After Gastric Bypass Surgery" American Association of Neurological Surgeons. Mar. 9, 2005.
Tsai et al "Outcomes of Common Peroneal Nerve Lesions After Surgical Repair with Acidic Fibroblast Growth Factor" The Journal of Trauma: Injury, Infection and Critical Care vol. 66, pp. 1379-1384. 2009.

* cited by examiner

*Primary Examiner* — Gregory S Emch
*Assistant Examiner* — Adam M Weidner
(74) *Attorney, Agent, or Firm* — Cesari and McKenna, LLP

(57) ABSTRACT

The present invention provides for treating neurodegeneration caused by nerve compression syndrome or entrapment neuropathy comprising administering human acidic fibroblast growth factor (aFGF), fibrinogen, aprotinin and divalent calcium ions to a subject in need thereof.

7 Claims, 1 Drawing Sheet

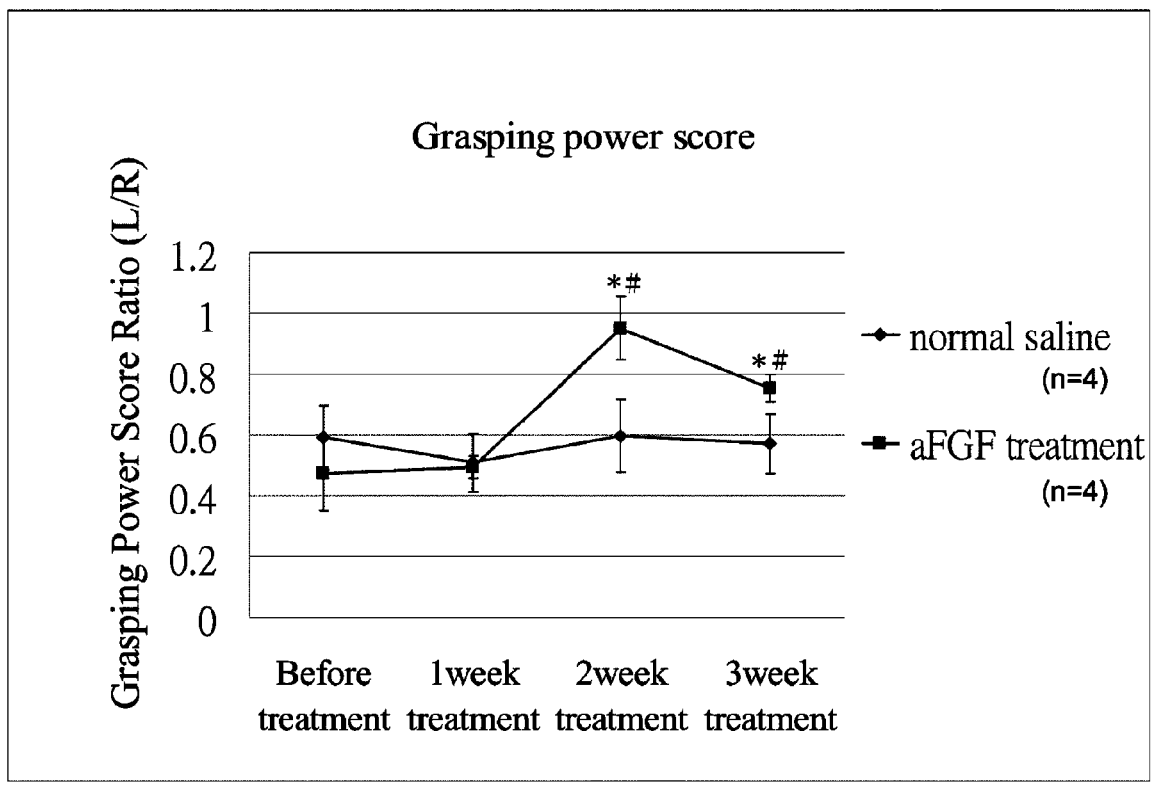

```
                       SEQUENCE LISTING

<160> NUMBER OF SEQ ID NOS: 1

<210> SEQ ID NO 1
<211> LENGTH: 135
<212> TYPE: PRT
<213> ORGANISM: Homo sapiens

<400> SEQUENCE: 1

Ala Asn Tyr Lys Lys Pro Lys Leu Leu Tyr Cys Ser Asn Gly Gly His
1               5                   10                  15

Phe Leu Arg Ile Leu Pro Asp Gly Thr Val Asp Gly Thr Arg Asp Arg
            20                  25                  30

Ser Asp Gln His Ile Gln Leu Gln Leu Ser Ala Glu Ser Val Gly Glu
        35                  40                  45

Val Tyr Ile Lys Ser Thr Glu Thr Gly Gln Tyr Leu Ala Met Asp Thr
    50                  55                  60

Asp Gly Leu Leu Tyr Gly Ser Gln Thr Pro Asn Glu Glu Cys Leu Phe
65                  70                  75                  80

Leu Glu Arg Leu Glu Glu Asn His Tyr Asn Thr Tyr Ile Ser Lys Lys
                85                  90                  95

His Ala Glu Lys Asn Trp Phe Val Gly Leu Lys Lys Asn Gly Ser Cys
            100                 105                 110

Lys Arg Gly Pro Arg Thr His Tyr Gly Gln Lys Ala Ile Leu Phe Leu
        115                 120                 125

Pro Leu Pro Val Ser Ser Asp
130                 135
```

METHOD FOR REPAIRING NEURODEGENERATION

CROSS-REFERENCE TO RELATED APPLICATION PARAGRAPH

This application claims the benefit of U.S. Provisional Application No. 61/233,987 filed on Aug. 14, 2009, the content of which is hereby incorporated by reference in its entirety.

BACKGROUND OF THE INVENTION

Nerve compressive syndrome, also known as entrapment neuropathy, is a medical condition caused by direct pressure, structural changes in the nerve or adjacent tissues or mechanically injury on a single nerve. Its symptoms include pain, tingling, numbness, and muscle weakness. The symptoms affect just one particular part of the body, depending on which nerve is affected. Although a well known example is compression of the median nerve at the wrist (carpal tunnel syndrome), other nerves, such as the ulnar nerve at the wrist or the elbow and the spinal nerve roots at the vertebral foramen, are vulnerable. Long term effect of nerve compression may lead to neuron degeneration and the loss of neural function.

Decompression surgery is a regular therapeutic method to remove the compressive source, such as bone or cartilage, to release a pressure and mitigate the neuropathic pain. After surgery, the symptoms may resolve completely, but if the compression was sufficiently severe or prolonged, the nerve may not recover fully and some symptoms may persist. Moreover, the functional recovery of the patients after the surgery will need longer time to be achieved. In most cases, the degeneration of nerve fiber cannot be repaired with the decompression surgery.

Therefore, there is still a need on discovering a method for functional improvement or recovery of degenerated nerves in the early stage of entrapment neuropathy or after the decompression surgery.

BRIEF SUMMARY OF THE INVENTION

The invention unexpectedly discovers that acid fibroblast growth factor (aFGF) plays a critical role in neural regeneration. When administering aFGF to a subject suffering nerve compressive syndrome, it was observed functional recovery of the degenerative or injured nerve. In comparison with the traditional decompression surgery, injection aFGF is more effective and safer treatment.

Accordingly, the invention is to provide a method for treating neurodegeneration caused by nerve compression syndrome or entrapment neuropathy comprising administering human acidic fibroblast growth factor (aFGF) to a subject in need thereof.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings.

In the drawings:

FIG. 1 is a diagram showing the grasping power test performed by the rats having compression surgery administered saline or human aFGF by foramen magnum injection. * indicates the significant different between aFGF treatment group and control group ($p<0.05$). # indicates the significant different between pre-treatment and post-treatment of aFGF ($p<0.05$).

DETAILED DESCRIPTION OF THE INVENTION

As used herein, the article "a" or "an" means one or more than one (that is, at least one) of the grammatical object of the article, unless otherwise made clear in the specific use of the article in only a singular sense.

The invention is to provide a method for treating neurodegeneration caused by nerve compression syndrome or entrapment neuropathy comprising administering a fibrin glue mixture comprising human acidic fibroblast growth factor (aFGF) to a subject in need thereof.

The term "nerve compression syndrome" or "entrapment neuropathy" as used herein refers to peripheral-nerve dysfunction that is due to localized interference of microvascular function and structural changes in the nerve or adjacent tissues. Nerve compression syndrome may be compressed by prolonged or repeated external force, such as sitting with one's arm over the back of a chair (radial nerve), frequently resting one's elbows on a table (ulnar nerve), or an ill-fitting cast or brace on the leg (peroneal nerve). As the compression becomes more severe over time, focal demyelination occurs, followed by axonal damage, and finally scarring. Moreover, some conditions cause nerves to be particularly susceptible to compression. These include diabetes, in which the blood supply to the nerves is already compromised, rendering the nerve more sensitive to minor degrees of compression.

Common nerve compression syndromes include herniated intervertebral disc, cervical nerve compression syndrome, thoracic outlet syndrome, and carpal tunnel syndrome. Other nerve compression syndromes may include but not limited to anterior interosseous syndrome, pronator teres syndrome, ligament of Struthers syndrome, cubital tunnel syndrome, Guyon's canal syndrome, radial nerve compression, posterior interosseous nerve entrapment, Wartenberg's syndrome, suprascapular nerve entrapment, peroneal nerve compression, tarsal tunnel syndrome, meralgia paraesthetica, iliohypogastric nerve entrapment, obturator nerve entrapment, pudendal nerve entrapment, and abdominal cutaneous nerve entrapment syndrome.

The term "human aFGF" as used herein refers to a native human aFGF or any modified peptide from the native human aFGF. The modified peptide may be obtained such as by one or more deletions, insertions or substitutions or combination thereof in the native human aFGF. In one embodiment of the invention, the modified human aFGF is a peptide comprising a native human aFGF shortened by a deletion of 20 amino acids from N-terminal of the native human aFGF, and an addition of Alanine before the shortened native aFGF. For example, the human aFGF may be a peptide having the amino acid sequence of SEQ ID NO:1, which is described in U.S. application Ser. No. 12/482,041, and hereby incorporated by reference herein in its entirety.

According to the invention, the human aFGF may be constituted into any form suitable for the mode of administration selected. Preferably, the human aFGF is administered topically, intraneurally, or intramuscularly. According to the invention, the skilled person in the art may easily determine the administrative pathway and the dosage dependent on his experiments or the physiological status of the patents suffering nerve compression syndromes, i.e. aging, body weight, severity, or dosage. In an embodiment of the invention, 0.1 mg/ml human aFGF were injected into the left adductor hallucis muscles.

It is known that polypeptide or protein may easily degrade in vivo. In order to prolong the effect of human aFGF in a subject, human aFGF may be included in any carriers or compositions for sustained release. For example, fibrin glue has been successfully used in a wide range of surgical fields such as skin graft fixation, nerve repair, cartilage reattachment and microvascular anastomoses. Researches also demonstrated sustained release of an active agent from fibrin glue for a longer period.

Thus, in one example of the present invention, human aFGF is contained in a fibrin glue mixture and administered to the subject suffering nerve compression syndrome or entrapment neuropathy. The concentration of the aFGF in the fibrin glue mixture is preferably about 0.01 mg/ml to 100 mg/ml. In one embodiment of the invention, the fibrin glue mixture contained 0.1 mg/ml aFGF when administered by adductor hallucis muscle injection. In another embodiment of the invention, the fibrin glue mixture contained 0.04 mg/ml aFGF when administered by foramen magnum injection. For those skilled in the art, the therapeutically effective amount, as well as dosage and frequency of administration, may easily be determined according to their knowledge and standard methodology of merely routine experimentation based on the present disclosure.

The fibrin glue mixture of the present invention referred to a pharmaceutical composition contains human aFGF, fibrinogen, aprotinin and divalent calcium ions, which may provide the effect of biocompatibility and sustained release. In one example of the invention, the divalent calcium ions can be any calcium ion sources, such as those provided by addition of calcium chloride or calcium carbonate.

According to the invention, the fibrin glue mixture comprises 0.01-100 mg/ml of human aFGF, and a fibrin glue containing 10-1000 mg/ml of fibrinogen, 10-500 KIU/ml of aprotinin and 0.1-10 mM of calcium chloride. In one example of the present invention, in order to provide better coagulation effect, the fibrin glue mixture may further comprise 10-100 IU/ml thrombin.

The fibrin glue mixture of the present invention may be constituted into any form suitable for the mode of administration selected. Preferably, the fibrin glue mixture is administered topically, intraneurally, or intramuscularly. According to the invention, the skilled person in the art may easily determine the administrative pathway dependent on his experiments or the physiological status of the patents suffering nerve compression syndromes, i.e. aging, body weight, severity, or dosage.

According to the invention, a neurodegenerative animal model was designed to demonstrate the effect in promoting nerve fiber outgrowth and functional recovery. In one embodiment of the invention, the left cervical dorsal root ganglion (DRG) was ligated with nylon suture 8-0. One week after ligation injury, total 0.6 µg aFGF in 6 µl normal saline were injected into the left adductor hallucis muscles.

In another embodiment of the invention, one week after ligation injury, 5 µl of fibrin glue mixture comprising 0.04 mg/ml (0.2 µg aFGF in 5 µl saline), 10 mg/ml of fibrinogen, and 200 KIU/ml of aprotinin was injected directly into foramen magnum of the rats conducted the surgery. Five minutes after the first injection, 10 µl of supplemental composition comprising 0.45 mM of calcium chloride and 10 IU/ml thrombin was injected into foramen magnum by the same injector.

The functional improvement was determined by a grasping power test. As the result thus obtained from the test on 2 and 3 weeks after the treatment, the group administered with aFGF had a better effects on recovering neural function in terms of a significantly high grasping power ratio (injury side-L/normal side-R) than the sham control group (administered with saline only). Given the results, the present invention provides an unexpected treatment for recovery of neural function.

As neural regeneration is time-consuming, continuous administration is required for repairing neural degeneration. In one example of the invention, it was suggested to administer the subject the fibrin glue mixture comprising human aFGF once a month. Anyone skilled in the art can determine the dose regiment according to the standard methods and common knowledge and the performance of the subject to be administered.

The present invention is more specifically explained by the following example. However, it should be noted that the present invention is not limited to these examples in any manner.

EXAMPLE aFGF Rescues Neural Function in a Rat Model of Compression Neuropathy

Animals

A total of twenty adult female Sprague-Dawley rats, aged between 8 and 10 weeks, body weight 250-300 g were used. The animals were operated on a heating pad under general halothane anesthesia (1.0 liter/min to keep the breathing rate at approximately 60/min). Rectal temperatures were monitored and maintained during surgery. Bipolar electrocauterization was used to minimize bleeding. Antibiotics were injected subcutaneously before the operation and one daily for 1 week afterward. After the operation, animals were kept in ventilated, humidity- and temperature-controlled rooms with a 12/12-h light/dark cycle.

Compression Surgery in Rats

The rats were placed in a prone position and their C4-C8 vertebrae were exposed. Left C4 to C7 hemilaminectomies were carried out. While under the microscope, the left C5 to C7 cervical roots were identified and followed after the overlying facets had been removed by drilling slightly more laterally in these segments. The dura was then carefully opened and the C5 to C7 nerve roots were pulled tight and the C5, C6 and C7 section of left cervical dorsal root ganglion (DRG) were exposed and ligated with the distal segment by nylon suture 8-0. After the surgery, these rats were divided into two experimental groups.

In Group A, the rats were divided into a sham control group (treated with saline, n=6), and aFGF group (treated with 0.6 µg aFGF in 6 n=5). One week after the compression surgery, the rats were anesthetized with isoflurane and kept on the warm pad to maintain their body temperature, total 0.6 µg aFGF in 6 µl normal saline were slowly injected intramuscularly into adductor hallucis muscles (from $1^{st}$ to $4^{th}$ pads, 1.5 µl/pad) in aFGF treatment group, while control group was injected with normal saline. The neural function recovery was estimated by grasping power test (Table 1).

Alternatively in Group B, the rats were also divided into two groups: a sham control group treated with saline (n=4), and aFGF treatment group (0.2 µg aFGF/in 5 saline, n=4). One week after the compression surgery, aFGF mixed with 5 µl of cocktail solution containing 1.5 mg fibrinogen (Beriplast P, Germany), apotinin solution (200 KIU/ml, 20 µl) and HBSS (Hank's balanced solution, 80 µl) was slowly injected into the foramen magnum in aFGF treatment group, while control group was injected with normal saline mixed with 5 µl of cocktail solution. Five minutes after the injection of cocktail solution with aFGF or saline, 10 µl of second solution containing 0.45 mM of calcium chloride and 10 IU/ml thrombin was injected into the foramen magnum, and removed the injectors a few seconds later. The neural function recovery was also estimated by grasping power test (FIG. 1).

Grasping Power Test

The grasping power test was a modification of the method of Bertelli and Mira (J. A. Bertelli et al., and J. C. Mira, Neurosci Methods 58:151-5, 1995). For the assessment of grasping strength, a bar of wires was connected to an ordinary electronic balance. Both forepaws were tested, testing one forepaw at a time. The untested forepaw was temporarily prevented from grasping by wrapping it with adhesive tape, and the tested forepaw was kept free. The rats were allowed to grasp the bar while being lifted by the tail with increasing firmness until they loosened their grip, and the grasping power was scored. The grasping power index is the ratio of injured side/normal side (injury side-L/normal side-R). Higher the score, better the functional recovery.

Table 1 demonstrated grasping result of Group A injected intramuscularly into adductor hallucis muscle. It was observed that the rats of aFGF treatment group performed better grasping power than those in the control group.

TABLE 1

| Group | Rat No. | pre-treat-1 d | post-treat-6 d | post-treat-15 d | post-treat-40 d |
|---|---|---|---|---|---|
| Grasping Power Test Result of Group A (Intramuscularly Injection) | | | | | |
| aFGF | A0055 | 0.647 | 0.743 | — | 0.830 |
| | A0056 | 0.714 | 0.366 | 0.950 | 0.874 |
| | A0061 | 0.620 | — | 0.604 | 1.060 |
| | A0062 | 0.606 | — | 0.815 | 0.750 |
| | A0065 | 0.296 | — | — | 0.945 |
| | AVERAGE | 0.576 | 0.554 | 0.790 | 0.874 |
| | | pre-treat-2 d | post-treat-5 d | post-treat-14 d | post-treat-44 d |
| Saline | A0057 | 0.433 | 0.409 | 0.721 | 0.382 |
| | A0058 | 0.686 | 0.540 | 0.433 | 0.895 |
| | A0059 | 0.353 | 0.448 | — | 0.579 |
| | A0060 | 0.479 | 1.078 | 0.715 | 1.077 |
| | A0063 | 0.581 | — | — | 0.767 |
| | A0064 | 0.565 | — | — | 1.234 |
| | AVERAGE | 0.516 | 0.619 | 0.623 | 0.733 |

The results of grasping power test for Group B was shown in FIG. 1. Two tailed Student's test was performed to examine statistic significance with respect to the difference in grasping power between aFGF treatment group and control group, or between pre-treatment and post-treatment of aFGF. In the FIG. 1, the score of the rats administered aFGF was significantly higher than those administered saline on the 2 week and 3 week after the treatment (*, $p<0.05$). On the other hand, the score of the rats administered aFGF after 2 week and 3 week were both significantly higher than those before the treatment of aFGF (#, $p<0.05$). These studies indicated that administering a subject having chronically/acutely compressed or mechanically injured nerves aFGF by the foramen magnum, could rescue neural function. It is a breakthrough in the current filed of treating neural degeneration caused by nerve compression syndrome.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A method for treating neurodegeneration caused by nerve compression syndrome or entrapment neuropathy comprising administering a human acidic fibroblast growth factor (aFGF) as the sole therapeutic agent to a subject in need thereof, wherein the human aFGF is mixed with fibrinogen, aprotinin and divalent calcium ions to form a fibrin glue mixture and then administered intraneurally.

2. The method according to claim 1, wherein the nerve compression syndrome or entrapment neuropathy is caused by chronic compression, acute compression, or a mechanical injury.

3. The method according to claim 1, wherein the nerve compression or entrapment neuropathy is caused by herniated intervertebral disc, cervical nerve compression syndrome, thoracic outlet syndrome, or carpal tunnel syndrome.

4. The method according to claim 1, wherein the human aFGF comprises a deletion of the first 20 amino acids from N-terminus of the native human aFGF followed by an addition of Alanine at the N-terminus of the shortened native aFGF.

5. The method according to claim 1, wherein the divalent calcium ions are provided by the addition of calcium chloride or calcium carbonate.

6. The method according to claim 1, wherein the fibrin glue mixture comprises 0.01-100 mg/ml of human aFGF, 10-1000 mg/ml of fibrinogen, 10-500 KIU/ml of aprotinin and 0.1-10 mM of calcium chloride.

7. The method according to claim 1, wherein the fibrin glue mixture comprises 0.04 mg/ml human aFGF, 10 mg/ml of fibrinogen, 200 KIU/ml of aprotinin and 0.45 mM of calcium chloride.

* * * * *